United States Patent [19]

Amano

[11] Patent Number: 5,423,747
[45] Date of Patent: Jun. 13, 1995

[54] MEDICAL PUMP DRIVE

[75] Inventor: Nobuhiko Amano, Nakai, Japan

[73] Assignee: Terumo Kabushiki Kaisha, Tokyo, Japan

[21] Appl. No.: 184,449

[22] Filed: Jan. 21, 1994

[30] Foreign Application Priority Data

Jan. 22, 1993 [JP] Japan .................................. 5-008681

[51] Int. Cl.⁶ .............................................. A61M 1/36
[52] U.S. Cl. .......................................... 604/65; 604/30; 604/31; 604/50; 604/118; 604/131; 604/151; 604/246; 128/DIG. 12; 128/DIG. 13
[58] Field of Search .......................... 604/4, 65, 5, 6, 7, 604/27, 30, 31, 35, 50, 118, 131, 151, 246; 128/DIG. 12, DIG. 13

[56] References Cited

U.S. PATENT DOCUMENTS 4,401,431 8/1983 Arp ........................................... 604/6
4,995,268 2/1991 Ash et al. ................................. 604/4
5,171,212 12/1992 Buck et al. .

Primary Examiner—C. Fred Rosenbaum
Assistant Examiner—N. Kent Gring
Attorney, Agent, or Firm—Burns, Doane, Swecker & Mathis

[57] ABSTRACT

A medical pump drive for automatically displaying not only the flow rate of circulating blood but also blood flow rate per surface area of the body of a patient in a medical treatment such as extracorporeal circulation includes at least a pump driving circuit, an ultrasonic transceiver and ultrasonic oscillator for measuring flow rate of the blood conveyed by a pump, a CPU, to which values of height and weight of a patient are entered, for calculating the body surface area of the patient as well as the blood flow rate per body surface area of the patient based upon the blood flow rate and body surface area obtained, an LCD for displaying the calculated blood flow rate per body surface area, and an LED for displaying the blood flow rate obtained.

6 Claims, 5 Drawing Sheets

MEDICAL PUMP DRIVE

BACKGROUND OF THE INVENTION

This invention relates to a medical pump driver and, more particularly, to a medical pump driver for driving a pump in order to convey a fluid within a fluid flow channel that includes a medical apparatus, wherein the pump drive has at least means for measuring and displaying blood flow rate per surface area of the patient.

In medical treatment by extracorporeal circulation or assisted circulation using a medical device such as an artificial organ inclusive of an artificial lung, centrifugal pumps have recently come to be utilized frequently as means for conveying blood or medicine such as Ringer's solution. The characteristic of a centrifugal pump is such that the amount of discharge varies owing to a change in after-load or a change in the internal pressure of the blood circuit. As a result, it is necessary to continuously control the flow of blood or the like in the apparatus that performs the extracorporeal circulation or assisted circulation of blood. In order to accurately ascertain the flow rate of blood in such an apparatus, use is made of a flowmeter that utilizes electromagnetic force or ultrasonic wave. Furthermore, in order to perform control accurately, a method of controlling the rotational speed of the centrifugal pump and a method of correcting the flow velocity and flow rate of the fluid have been proposed.

In medical treatment by the method of extracorporeal circulation or assisted circulation, the blood flow channels of, say, an extracorporeal circulation apparatus such as an artificial lung include a large number of complicated, cramped passages of a hollow-fiber type artificial lung, tubes and connectors. Accordingly, priming methods for removing air bubbles that have attached themselves to these passages also have been proposed.

However, patients that undergo treatment by extracorporeal circulation or assisted circulation in actual research or at clinical sites have body sizes that differ from one to another. When extracorporeal circulation or the like is carried out, therefore, the absolute flow rate of blood circulated naturally differs from patient to patient. Accordingly, at locations where such equipment is employed, use is made of blood flow rate per surface area of the body of the patient as a standardized indicator of blood flow rate. This is to deal with the difference in blood flow rate from one patient to another.

In such case, the conventional method of obtaining blood flow rate per body surface area on site involves calculating body surface area in advance utilizing the Du Bois formula based upon the height and weight of the patient, and using a flowmeter or the like to measure the flow rate of the fluid such as blood circulating extracorporeally. The values of flow rate outputted by the flowmeter moment by moment are read by a monitor or the like and the blood flow rate per body surface area is calculated moment by moment on site. Problems that result are delays in dealing with changes in blood flow rate, considerable labor on the part of the operator and a great deal of human intervention.

SUMMARY OF THE INVENTION

Accordingly, an object of the present invention is to provide a medical pump drive for automatically displaying not only the flow rate of circulating blood but also blood flow rate per surface area of the body of a patient in a medical treatment such as extracorporeal circulation.

According to the present invention, the foregoing object is attained by providing a medical pump drive for driving a pump in order to convey blood in a fluid flow channel that includes a medical device, comprising pump driving means for driving the pump, blood measuring means for measuring flow rate of the blood conveyed by the pump, calculating means for calculating blood flow rate per body surface area of a patient based upon the blood flow rate obtained by the blood measuring means, and display means for displaying the blood flow rate per body surface area obtained by the calculating means.

In a preferred embodiment, the medical pump drive includes input means for entering values of height and weight of the patient, and arithmetic means for calculating body surface area based upon the values of height and weight entered by the input means.

In accordance with the present invention as described above, body surface area is calculated upon entering the height and weight of a patient before the pump is driven to circulate blood extracorporeally or during the driving of the pump, the blood measuring means that measures the blood flow rate is actuated and the blood flow rate per body surface area is calculated from the blood flow rate and body surface area, thereby providing a display of blood flow rate per body surface area of the patient undergoing extracorporeal circulation.

The invention is particularly advantageous since it is possible to deal rapidly with adjustment of flow rate of extracorporeally circulating blood based upon blood flow rate per body surface area in actual research or at a clinical site.

Furthermore, since body surface area is calculated merely by entering the values of height and weight of the patient, the calculation of blood flow rate per body surface area can be performed in a shorter period of time without extra labor on the part of the operator.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Preferred embodiments of the present invention will now be described in detail in accordance with the accompanying drawings.

Figure 1:
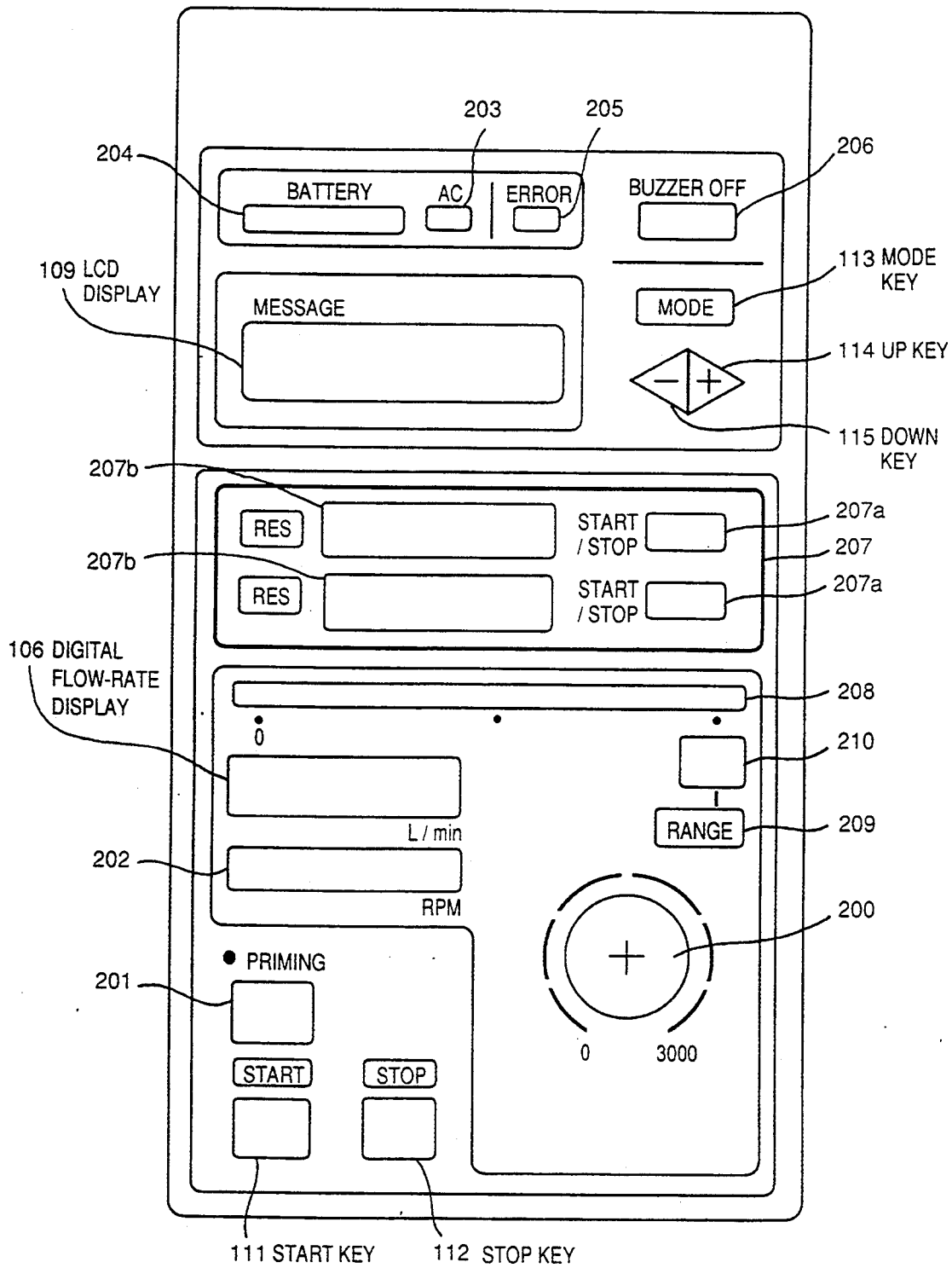
FIG. 1 is a top view illustrating the arrangement of the control panel of a medical pump drive serving as a typical embodiment of the present invention.

FIG. 1 is a top view illustrating the arrangement of a control panel on a medical pump drive representing a typical embodiment of the present invention. The control panel is provided with a START key 111 for commanding the start of pump drive, a STOP key 112 for commanding the termination of pump drive, a switch 201 for a priming operation, an LED display 106 for displaying the flow rate of a fluid that flows through an extracorporeal circulation circuit, a display 202 for displaying the rotational speed (RPM) of a motor that drives a centrifugal pump, described later, a speed regulating dial 200 for freely regulating the rotational speed of the motor driving the centrifugal pump, an LCD display 109 for displaying various messages for the operator, e.g., the height and weight of the patient, a set value of body surface area and blood flow rate per body surface area of the patient during drive of the apparatus, a MODE key 113 for selecting the contents of messages displayed on the LCD display 109, and an UP key 114 and down key 115 for setting the weight, height and body surface area of the patient to any value. The fluid handled by the medical pump of this embodiment is blood. However, this should be interpreted in a broad sense to include blood components such as blood plasma, a concentrated solution of red blood cells and a concentrated solution of platelets.

Further, the upper part of the control panel is provided with an AC indicator 203 for indicating that AC power has been introduced to the medical pump drive, a battery indicator 204 for indicating the remaining life of a battery serving as an emergency power supply for back-up in the event of a power failure, an error lamp 205 for giving a warning indication to the effect that blood flow rate has exceeded a predetermined threshold value, and a buzzer OFF switch 206 for turning off a buzzer (not shown) which emits an audible tone when the error lamp 205 lights.

The central part of the control panel is provided with a stopwatch 207 whereby any time can be measured during the operation of the pump drive of this embodiment. The stopwatch 207 internally incorporates two timers each of which is capable of measuring time independently of the other. The stopwatch 207 includes start/stop switches 207a for commanding start/stop of respective ones of the stopwatches, and displays 207b for displaying the times measured by respective ones of the two timers.

An LED indicator 208 for displaying an analog bar of flow rate based upon a change in quantity of light commensurate with blood flow rate is provided above the LED display 106. The display scale of the LED indicator 208 is set by a display-scale setting switch 209 that is capable of changing the display scale in three stages. The value set is displayed by an LED 210. The display scale is set in dependence upon the flow rate. For example, if the display scale is set to stage "1" by the display-scale setting switch 209, the LED indicator 208 will light over its entire length from the left end to the right end when the flow rate reaches 10 l/min. If the display scale is set to stage "2" by the display-scale setting switch 209, the LED indicator 208 will light over its entire length from the left end to the right end when the flow rate reaches 5 l/min. Further, if the display scale is set to stage "3" by the display-scale setting switch 209, the LED indicator 208 will light over its entire length from the left end to the right end when the flow rate reaches 2 l/min.

Figure 2:
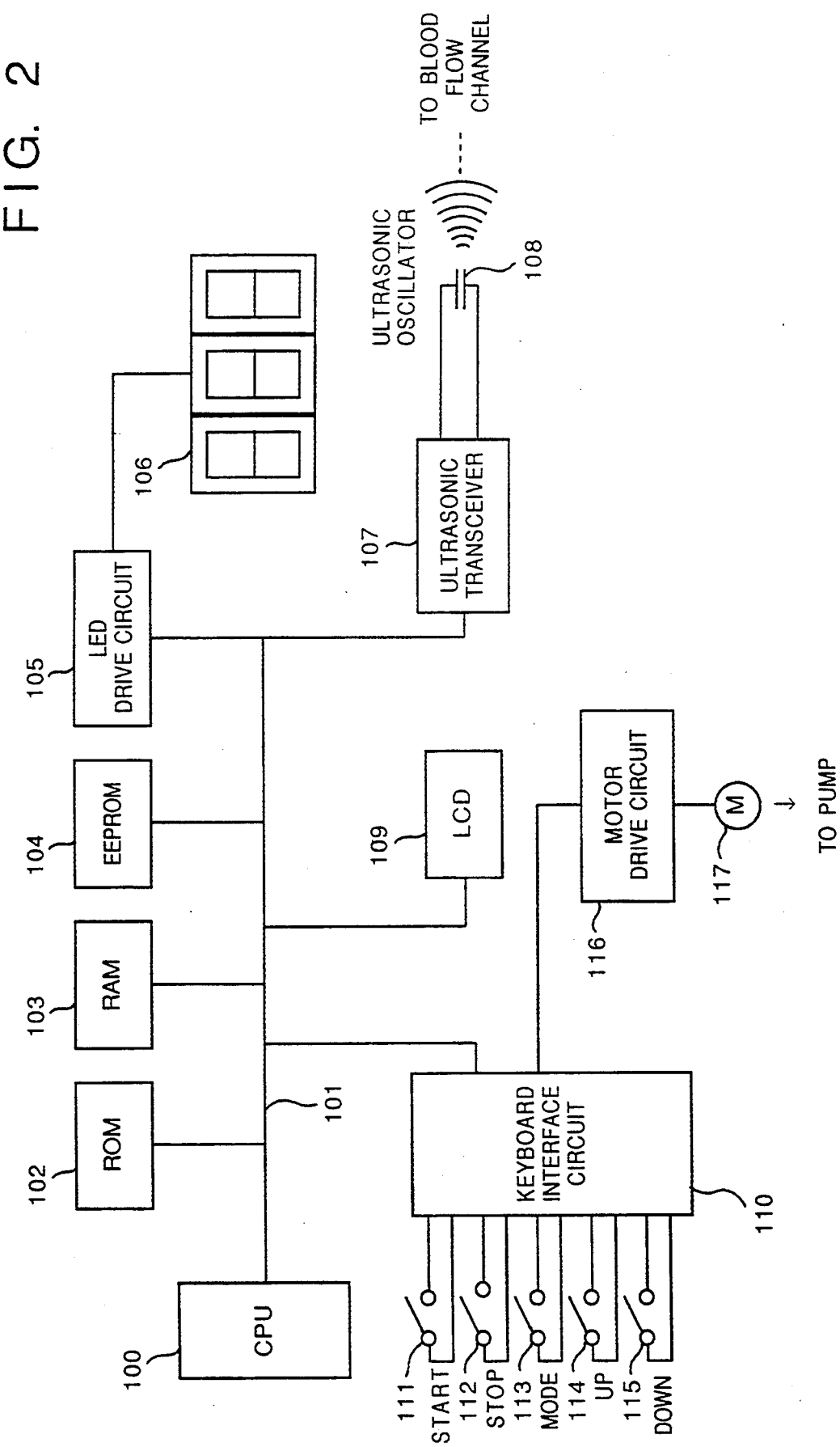
FIG. 2 is a circuit block diagram illustrating mainly circuitry for calculating blood flow rate per body surface area.

FIG. 2 is a block diagram illustrating the construction of a circuit (hereinafter referred to as a "blood flow-rate calculating circuit") for measuring blood flow rate and calculating blood flow rate per body surface area in the medical pump drive serving as a typical embodiment of the present invention. The blood flow-rate calculating circuit is equipped with a CPU (central processing unit) 100 for centrally executing measurement and calculation of blood flow rate as well as display instructions. The CPU 100 is connected to each component of the apparatus via a CPU bus 101.

A ROM (read-only memory) 102 stores programs for the purpose of executing an operation for calculating flow rate by multiplying blood flow velocity, which is measured by a blood flow-velocity measuring circuit comprising an ultrasonic transceiver 107 and an ultrasonic oscillator 108, by the cross sectional area of the flow channel, an operation for calculating body surface area from the height and weight of the patient in accordance with the Du Bois formula, and an operation for calculating blood flow rate per body surface area of the patient from the above-mentioned blood flow rate and body surface area.

A RAM (random-access memory) 103 is used to temporarily store various data, which is necessary to calculate the blood flow rate per body surface area, such as the measured values of height and weight of the patient and values of blood flow rate calculated from time to time in the course of various operations.

An EEPROM (electrically erasable programmable read-only memory) 104 is a memory capable of being partially rewritten in order to store initial values of height and weight. It should be noted that the values of height and weight stored in the RAM 102 may be stored in the EEPROM 104 in order to be backed up.

An LED drive circuit 105 performs control in such a manner that the LED 106 will display the value obtained by measuring blood flow velocity using the ultrasonic transceiver 107 and ultrasonic oscillator 108 and operating upon the blood flow velocity to obtain the blood flow rate using the CPU 100.

The CPU 100 further controls a keyboard interface circuit 110 to receive various command signals outputted by the switches comprising the START key 111, the STOP key 112, the MODE key 113, the UP key 114 and the down key 115 and to send some of these command signals to the motor drive circuit 116. That is, though the output signals from all switches are sent to the CPU 100, the output signals from the START switch 111 and STOP switch 112 are sent also to the motor drive circuit 116.

When the motor 117 is driven by a command from the START key 111, the CPU 100 calculates blood flow rate from the blood flow-velocity data obtained from the ultrasonic transceiver 107 and controls the LED drive circuit 105 to display the results of calculation on the LED 106 as the occasion demands. These operations are performed based upon the programs stored in the ROM 102. In a mode for setting of a height value, a mode for setting of a weight value and a mode for setting of body surface area set by the UP key 114 or DOWN key 115, the CPU 100 reads in these initial values from the EEPROM 104 and, if necessary, allows each of these values to be revised again using the UP key 114 or DOWN key 115 and stores the revised values in the EEPROM 104 or RAM 103. The CPU 100 causes the LCD 109 to display these values in the respective modes. Further, the CPU 100 calculates the body surface area from the height value and weight value of the patient based upon the programs stored in the ROM 102 and displays these values on the LCD 109. Furthermore, the CPU 100 calculates the blood flow rate per body surface area from the value of blood flow rate and value of body surface area on the basis of the programs stored in the ROM 102 and displays the calculated value on the LCD 109.

Though which of the above-mentioned numerical values is displayed on the LCD 109 is selected by the MODE key 113, ordinarily the blood flow rate per body surface area is displayed.

The motor drive circuit 116 drives the motor 117 upon receiving a start signal outputted by the START key 111 and stops driving the motor 117 upon receiving a stop signal outputted by the STOP key 112. A variable resistor is connected to the motor drive circuit 116 and makes it possible to adjust the rotational speed of the motor while the displayed blood flow rate per body surface area is monitored.

Figure 3:
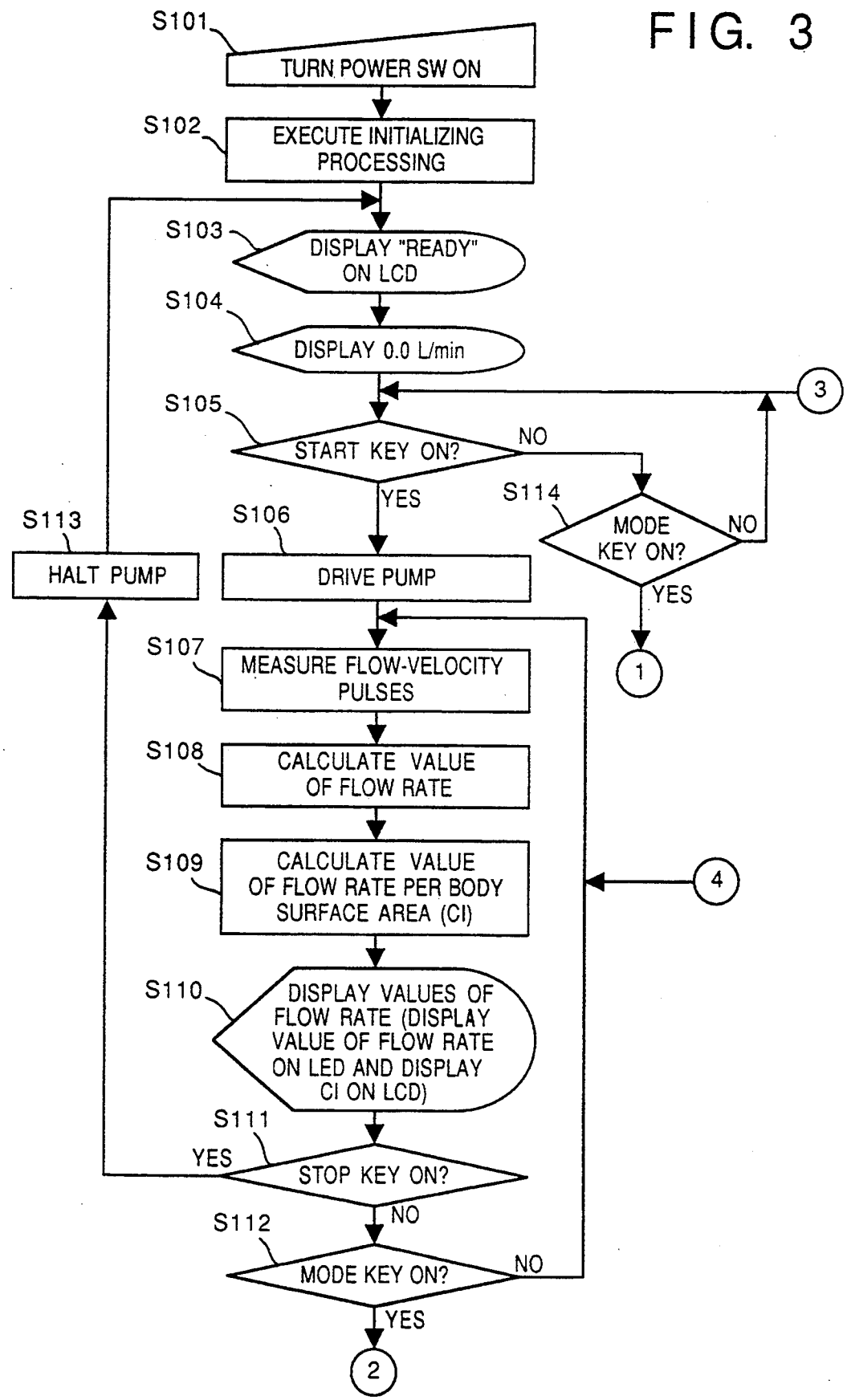
FIG. 3 is an overall flowchart illustrating an operation for calculating blood flow rate per body surface area.
Figure 4:
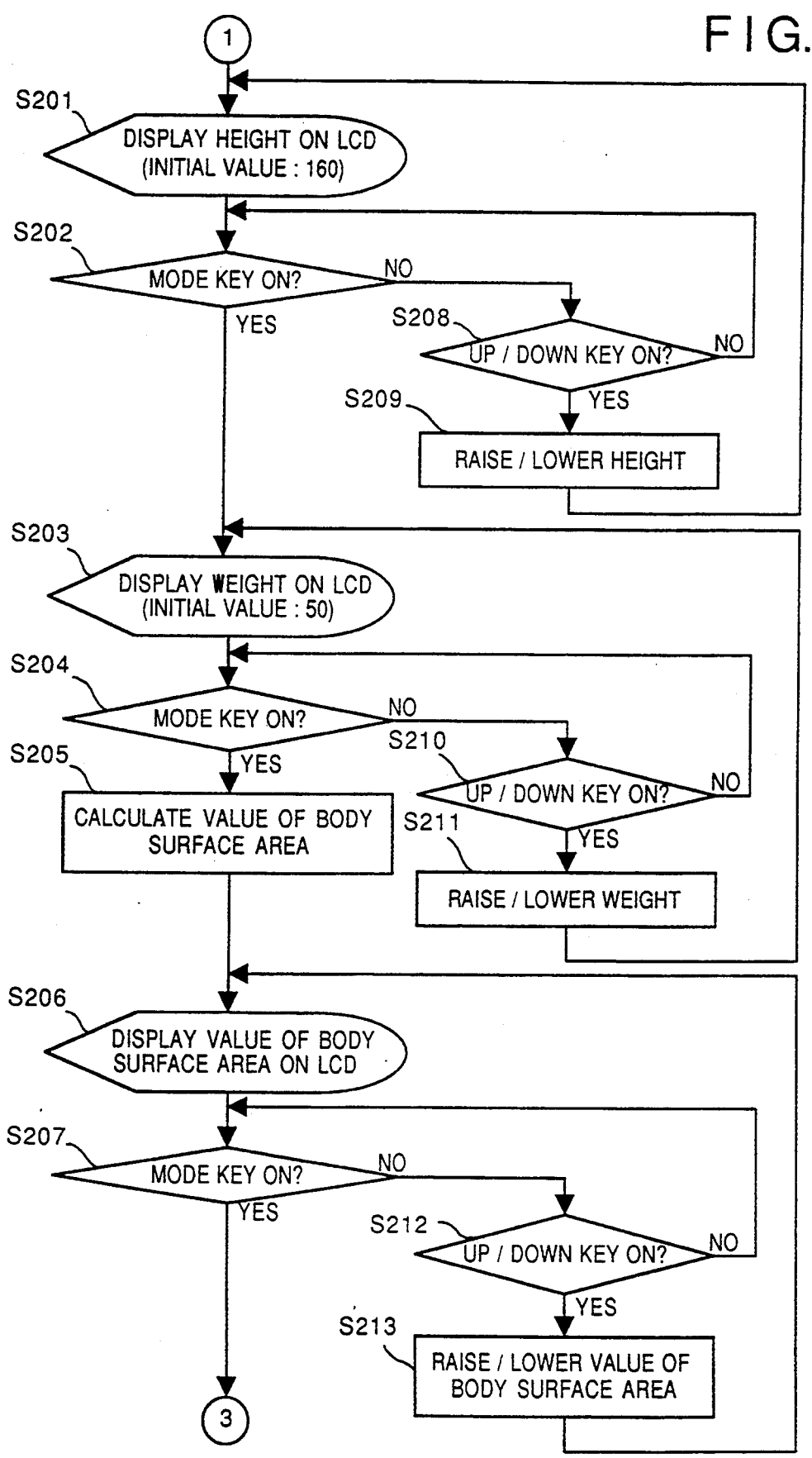
FIG. 4 is a flowchart illustrating an operation for calculating body surface area prior to pump drive.
Figure 5:
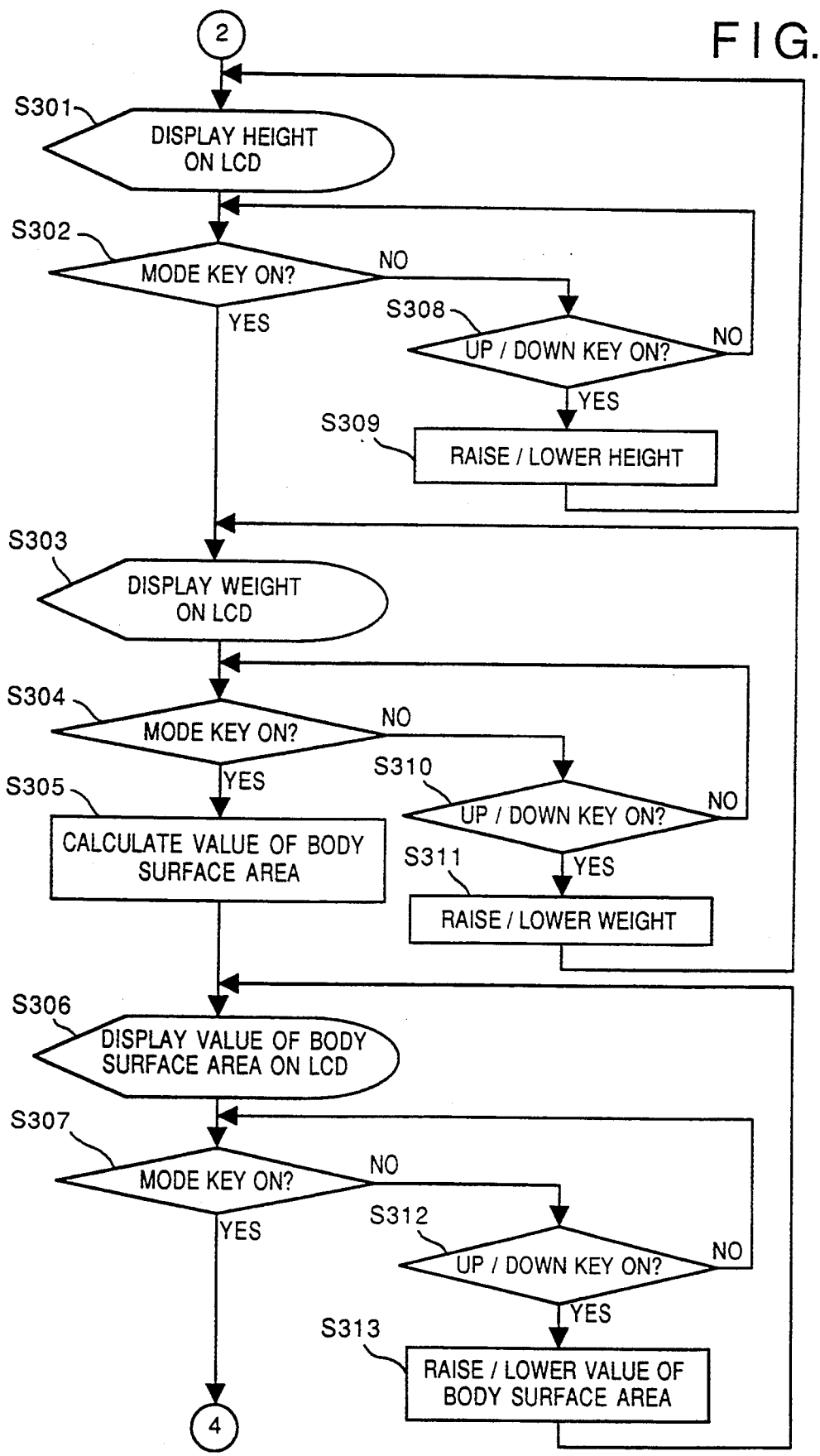
FIG. 5 is a flowchart illustrating an operation for calculating body surface area during pump drive.

The operation for calculating blood flow rate performed by the medical pump drive constructed as set forth above will now be described in detail with reference to the flowcharts of FIGS. 3 through 5.

First, when a power switch (not shown) is turned on (step S101), the CPU 100 executes initializing processing (step S102). The LCD 109 then displays "READY" (step S103) and the LED 106 displays 0.0 (l/min) (step S104).

In a case where body surface area is entered prior to driving of the pump, the START key 111 is not pressed (step S105). Instead, the MODE key 113 is pressed to change over the mode (step S114), and the height of the patient is displayed by the LCD 109 (step S201).

At this time "160 (cm)", for example, is displayed as the initial value. When the initially set value is not to be changed, the MODE key 113 is pressed to change over the mode (step S202) and the information displayed by the LCD 109 changes to a value of body weight (step S203). On the other hand, when the initially set value of height is to be changed, i.e., when the displayed value of "160 cm" is to be changed to another value, the UP key 114 or DOWN key 115 is pressed to raise or lower the value (step S208) and effect the change (step S209). In this embodiment, the value of height may be changed at intervals of 1 cm. However, it goes without saying that corrections may be made at intervals of 0.1 cm.

After the change in the value of height is made, the MODE key 113 is pressed to change over the mode (step S202), whereupon the LCD presents a display of body weight (step S203). At this time "50 (kg)", for example, is displayed as the initial value. When the initially set value is not to be changed, the MODE key 113 is pressed to change over the mode (step S204), whereupon body surface area is calculated from the set values of height and weight (step S205). The calculated value of body surface area is then displayed by the LCD 109 (step S206). On the other hand, when the initially set value of weight is to be changed, i.e., when the displayed value of "50 kg" is to be changed to another value, the UP key 114 or DOWN key 115 is pressed to raise or lower the value (step S210) and effect the change (step S211). In this embodiment, the value of weight may be changed at intervals of 1 kg. However, it goes without saying that corrections may be made at intervals of 0.1 kg.

Thus, when the MODE key 113 is pressed to change over the mode (step S204) after the body weight is changed, the calculation of body surface area is performed (step S205) based upon the set or changed values of height and weight and the calculated value is displayed by the LCD 109 (step S206).

When the value of body surface area obtained and displayed by the foregoing processing is not to be changed, processing returns to step S105, namely the state prevailing prior to driving of the pump, if the MODE key 113 is pressed to change over the mode (step S207).

In a case where it is desired to change the displayed value of body surface area or directly enter a value of body surface area, the MODE key 113 is not pressed and the mode is not changed over. Rather, the UP key 114 or DOWN key 115 is pressed to raise or lower the value (step S212) and change the body surface area to any value (step S213). Thereafter, the MODE key 113 is pressed to change over the mode (step S207) and processing returns to step S105, namely the state prevailing prior to driving of the pump.

Next, when the START key 111 is pressed (step S105), the motor rotates and the pump is driven (step S106). When the pump is driven and blood flows into the channel, flow-velocity pulses are measured (step S107) and the flow velocity of blood is measured in order to calculate the flow rate of blood. The value of blood flow rate is calculated (step S108) from the measured value of flow velocity and the cross sectional area of the flow channel at the point of measurement.

According to this embodiment, measurement of the flow rate of extracorporeally circulating blood is performed using an ultrasonic Doppler method in order to calculate the flow rate of blood. Ultrasonic waves produced by the ultrasonic oscillator 108 controlled by the ultrasonic transceiver 107 are emitted into the blood, and waves reflected by the blood are received as flow-velocity pulses. Since blood flows at a certain velocity, the frequency of the reflected waves received by the ultrasonic transceiver 107 is Doppler-shifted owing to the Doppler effect. Accordingly, the flow velocity of blood is obtained based upon this Doppler shift and the flow rate can be calculated by multiplying this value by the cross sectional area (already known) of the flow channel at the point of measurement.

Furthermore, the value of blood flow rate per body surface area (CI) is calculated from the values of body surface area and blood flow rate (step S109). The blood flow rate per body surface area is calculated by dividing the obtained blood flow rate by the body surface area obtained in the following manner:

The value of body surface area generally is found by the Du Bois formula. The Du Bois formula is written as follows:

$$S = H^{0.725} \times W^{0.425} \times k$$

where S (m²) represents the body surface area of the patient, H (cm) the height of the patient and W (kg) the body weight of the patient.

In the formula mentioned above, k is a constant that differs depending upon the race of the patient. For example, the constant is 0.007184 for Occidentals and 0.007246 for Japanese. The value of body surface area can be calculated by applying the values of height and weight of the patient and the above-mentioned constant to the Du Bois formula.

The value of blood flow rate calculated at this time is displayed by the LED 106, and the value of blood flow rate per body surface area is displayed by the LCD 109 (step S110). These displays are presented in real time.

When medical treatment or the like ends and the pump is to be halted, the STOP key 112 is pressed (step S111) to stop the pump (step S113). When the pump stops, the displays presented by the LCD 109 and LED 106 revert to a state prevailing immediately after initialization (steps S103~S104).

Next, processing will be described for a case in which the value of body surface area is calculated after driving of the pump by pressing the START key 111.

This is a case in which the CPU 100 executes initializing processing (step S102), the LCD 109 displays "READY" (step S103) and the LED 106 displays "0.0" (l/min) (S104), after which the START key 111 is pressed (step S105) to rotate the motor 117 and drive the pump (not shown) (step S106). When the pump 117 is driven and blood flows into the flow channel, the flow velocity of the blood is obtained by measurement of flow-velocity pulses (step S107), the value of blood flow rate is calculated from the value of flow velocity and the cross sectional area of the flow channel at the point of measurement (step S108), and the calculated value of blood flow rate is indicated by the LED 106 in real time (step S110), as already described.

When the MODE key 113 is pressed in order to set the value of body surface area under these conditions, the mode is changed over (step S112) and the initial value [e.g., 160 (cm)] of height is displayed by the LCD 109 (step S301).

When the initially set value of height is not to be changed, the MODE key 113 is pressed to change over the mode (step S302) and the LCD 109 presents a display of the initial value of body weight (step S303). On the other hand, when the initially set value [e.g., 160 (cm)] of height is to be changed, the UP key 114 or DOWN key 115 is pressed to raise or lower the value (step S308) and the value is changed (step S309).

When the MODE key 113 is pressed to change over the mode (step S302) after the value of height is changed, the LCD presents a display of body weight (step S303). At this time "50 (kg)" for example, is displayed as the initial value of body weight. If the initially set value is not to be changed, the MODE key 113 is pressed to change over the mode (step S304), the body surface area is calculated from the set values of height and weight (step S305) and the calculated value of body surface area is displayed by the LCD 109 (step S306). On the other hand, when the initially set value of weight is to be changed, i.e., when the displayed value of "50 kg" is to be changed to another value, the UP key 114 or DOWN key 115 is pressed to raise or lower the value (step S310) and effect the change (step S311).

Thus, when the MODE key 113 is pressed to change over the mode (step S304) after the value of body weight is changed, the calculation of body surface area is performed (step S305) based upon the set or changed values of height and weight, and the calculated value is displayed by the LCD 109 (step S306).

When the displayed value of body surface area is not to be changed, the MODE key 113 is pressed to change over the mode (step S307) and processing returns to the state of step S107, namely the state prevailing after driving of the pump. On the other hand, in a case where it is desired to change the displayed value of body surface area or directly enter a value of body surface area, the MODE key 113 is not pressed and the mode is not changed over. Rather, the UP key 114 or DOWN key 115 is pressed to raise or lower the value (step S312) and change the body surface area to any value (step S313). Thereafter, the MODE key 113 is pressed to change over the mode (step S307) and processing returns to step S107, namely the state after driving of the pump.

At this time, since blood is already flowing through the channel owing to driving of the pump, flow-velocity pulses are measured in real time (step S107) and the flow velocity of blood is calculated. Blood flow rate is calculated as necessary from this value of flow velocity and the cross sectional area of the flow channel at the point of measurement (step S108). However, calculation of the next value (CI) of blood flow rate per body surface area (step S109) is performed based upon the newly set or calculated values of body surface area and blood flow rate. The calculated value of blood flow rate is displayed by the LED 106, and the value of blood flow rate per body surface area is displayed by the LCD 109 (step S110). These displays are presented in real time.

Thus, in accordance with the present embodiment, ultrasonic waves are emitted into blood, blood flow velocity is obtained based upon the Doppler shift obtained from the reflected waves, and flow rate is calculated in real time by multiplying this value by the already known cross sectional area of the channel. Body surface area is calculated from initial values or optionally set values of patient height and weight, and the value of flow rate per body surface area can be displayed automatically based upon the calculated flow rate and body surface area. As a result, the time and labor involved in calculating values of blood flow rate per body surface area manually can be reduced and it is possible to deal rapidly with changes in blood flow rate.

Furthermore, since the indicator for values of flow rate, the indicator for the rotational speed of the pump drive motor and the dial for adjusting motor rotation are provided in close proximity to one another, the pump can be finely adjusted with regard to changes in blood flow rate while the user observes the two indicators.

As many apparently widely different embodiments of the present invention can be made without departing from the spirit and scope thereof, it is to be understood that the invention is not limited to the specific embodiments thereof except as defined in the appended claims.

What is claimed is:

1. A medical pump drive for driving a pump in order to convey blood in a fluid flow channel that includes a medical device, comprising:
   pump driving means for driving the pump;
   blood measuring means for realtime measurement of a flow rate of the blood conveyed by said pump;
   calculating means for calculating blood flow rate per body surface area of a patient based upon the blood flow rate obtained by said blood measuring means; and
   first display means for automatic and realtime display of the blood flow rate per body surface area obtained by said calculating means.

2. The pump drive according to claim 1, wherein said calculating means includes memory means for storing initial values of body height and body weight in order to calculate the body surface area;

input means for entering values of body height and body weight of the patient; and arithmetic means for calculating body surface area of the patient based upon the initial values or the values of body height and body weight entered by said input means.

3. The pump drive according to claim 2, wherein said calculating means further includes:

input control means for performing control in such a manner that said input means is capable of entering values of body height and body weight of the patient even before the pump is driven by said pump driving means or even during driving of the pump; and data feedback means for performing control in such a manner that said arithmetic means calculates the body surface area of the patient based upon the values of body height and body weight entered during driving of the pump.

4. The pump drive according to claim 1, wherein said blood measuring means includes:

ultrasonic wave emitting means for emitting ultrasonic waves into blood conveyed by said pump;

receiving means for receiving ultrasonic waves reflected by the blood; and arithmetic means for calculating flow velocity of the blood from a Doppler shift of frequency possessed by the reflected ultrasonic sound waves received by said receiving means.

5. The pump drive according to claim 1, further comprising pump drive control means for controlling said pump driving means so as to regulate flow rate of the blood conveyed by said pump.

6. The pump drive according to claim 1, further comprising second display means for displaying the blood flow rate, which has been calculated by said blood measuring means, on a monitor.

* * * * *

UNITED STATES PATENT AND TRADEMARK OFFICE
CERTIFICATE OF CORRECTION

PATENT NO. : 5,423,747
DATED : June 13, 1995
INVENTOR(S) : Nobuhiko AMANO

It is certified that error appears in the above-indentified patent and that said Letters Patent is hereby corrected as shown below:

In Column 3, line 65, delete "10 l/min." and insert -- 10 $\ell$/min. --.
In Column 4, line 1, delete "5 l/min." and insert -- 5 $\ell$/min. --.
In Column 4, line 5, delete "2 l/min." and insert -- 2 $\ell$/min. --.
In Column 5, line 33, delete "(l/min)" and insert -- ($\ell$/min) --.

In Column 7, line 20, delete "(l/min)" and insert -- ($\ell$/min) --.

Signed and Sealed this

Seventeenth Day of October, 1995

Attest:

BRUCE LEHMAN

*Attesting Officer*     *Commissioner of Patents and Trademarks*